(12) United States Patent
Picard et al.

(10) Patent No.: US 8,140,143 B2
(45) Date of Patent: Mar. 20, 2012

(54) WASHABLE WEARABLE BIOSENSOR

(75) Inventors: Rosalind W. Picard, Newton, MA (US); Clayton J. Williams, Heber City, UT (US); Richard Ribon Fletcher, Medford, MA (US); Hoda Eydgahi, Salisbury, MD (US); Ming-Zher Poh, Cambridge, MA (US); Oliver Orion Wilder-Smith, Natick, MA (US); Kyunghee Kim, Cambridge, MA (US); Kelly Dobson, Cambridge, MA (US); Jackie Chia-Hsun Lee, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 337 days.

(21) Appl. No.: 12/386,348

(22) Filed: Apr. 16, 2009

(65) Prior Publication Data

US 2010/0268056 A1  Oct. 21, 2010

(51) Int. Cl.
  *A61B 5/04* (2006.01)
(52) U.S. Cl. ........................ 600/388; 600/382
(58) Field of Classification Search .................. 600/372, 600/382, 386, 388–390, 393
  See application file for complete search history.

(56) References Cited

U.S. PATENT DOCUMENTS

| | | | |
|---|---|---|---|
| 2,829,638 | A | 4/1958 | Douglas |
| 3,870,034 | A * | 3/1975 | James ........................ 600/547 |
| 6,415,176 | B1 * | 7/2002 | Scheirer et al. ............... 600/547 |
| 2002/0032386 | A1 | 3/2002 | Sackner et al. |
| 2002/0038092 | A1 | 3/2002 | Stanaland et al. |

(Continued)

FOREIGN PATENT DOCUMENTS

| | | |
|---|---|---|
| EP | 1886707 A1 | 2/2008 |
| WO | 2009023937 A1 | 2/2009 |

OTHER PUBLICATIONS

M. Strauss et. al, The HandWave Bluetooth Skin Conductance Sensor. In J. Tao, T. Tan and R. Picard, editors, ACII, vol. 3784 of Lectures Notes in Computer Science, pp. 699-706 , Springer, 2005.

(Continued)

*Primary Examiner* — Linda Dvorak
*Assistant Examiner* — Brian M Antiskay
(74) *Attorney, Agent, or Firm* — Stephen Otis

(57) ABSTRACT

A washable, wearable biosensor that can gather sensor data, communicate the sensed data by wireless protocols, and permits the analysis of sensed data in real-time as a person goes about their normal lifestyle activities. The biosensor can be worn in multiple positions, can be put on or removed quickly without having to apply or remove gels and adhesives, and provides a snug, comfortable fit to gather data with minimal motion artifacts. The textile, wearable device can support integrated photoplethysmography, skin conductance, motion, and temperature sensors in a small wearable package. The supported sensors may be coupled to utilization devices by channel-sharing wireless protocols to enable the transmission of data from multiple users and multiple sensors (e.g. both sides of body, wrists or hands and feet, or multiple people). An on-board processor, or the receiving utilization device, can map patterns of the physiological and motion data to signals or alerts such as a likely seizure, drug craving, or other states that the wearer may exhibit or experience. The sensor data may be sent by wireless transmission and received by a mobile phone or other personal digital device, a computer, a favorite toy, or another wearable device. The sensors may include multiple photoplethysmographs and/or one or more EDAs which perform a time-domain measurement of skin conductance.

13 Claims, 18 Drawing Sheets

U.S. PATENT DOCUMENTS

| | | |
|---|---|---|
| 2002/0198574 A1 | 12/2002 | Gumpert |
| 2003/0004424 A1 | 1/2003 | Birnbaum |
| 2003/0117651 A1 | 6/2003 | Matraszek |
| 2004/0073121 A1 | 4/2004 | Sun |
| 2005/0107655 A1 | 5/2005 | Holzner |
| 2006/0069319 A1 | 3/2006 | Elhag et al. |
| 2006/0211934 A1* | 9/2006 | Hassonjee et al. ............ 600/372 |
| 2006/0293608 A1 | 12/2006 | Rothman et al. |
| 2008/0167535 A1* | 7/2008 | Stivoric et al. ................ 600/301 |
| 2008/0214089 A1 | 9/2008 | Vermac et al. |

OTHER PUBLICATIONS

T. Westeyn et. al, ActionGSR: A Combination Galvanic Skin Response-Accelerometer for Physiological Measurements in Active Environments, iscw, pp. 129-130, 2006 10th IEEE Internatinal Symposium on Wearable Computers, 2006.

R. Picard et al., The Galvactivator: A Glove that Senses and Communicates Skin Conductivity, Proc. of 9th International Conference on Human-Computer Interaction, pp. 1538-1542 (2001).

* cited by examiner

WASHABLE WEARABLE BIOSENSOR

FIELD OF THE INVENTION

This invention relates to physiological sensors.

BACKGROUND OF THE INVENTION

In many settings, it is helpful to be able to measure and monitor physiological data on a long-term, outpatient basis. Existing wireless devices have sensors that measure one or more of electrodermal activity (EDA), which is also known as galvanic skin response, heart rate (HR), heart rate variability (HRV), temperature and motion. One type of sensor used to measure HR and HRV is a photoplethysmograph (PPG).

However, existing wireless biosensor devices have a number of disadvantages. They are generally bulky, uncomfortable and poorly suited for long-term use on an outpatient basis. Nor are they well suited for long-term wear by infants or uncooperative patients, such as a patient with dementia who would tend to remove existing sensors. In addition, they are not well suited for ambulatory, long-term wear by animals.

Typically, existing EDA sensors have cumbersome electrodes. The measurement of skin conductance commonly requires clipping electrodes on the fingertips or using adhesive patches. This severely limits the user's ability to perform tasks requiring the hands. Also, long-term (e.g., weeks) of continuous wear using rubberized electrodes is uncomfortable, as is long-term use of standard metal medical electrodes and the adhesive pads used to apply them. Both of these tend to cause skin irritation when the skin does not breathe for many days of use.

In addition, existing devices are generally encased in relatively large plastic shell cases and are not comfortable or suitable for wearing for more than a few hours. Nor do they allow the wearer the freedom of movement typical of daily activity.

Moreover, existing systems with wireless connectivity generally exhibit a short battery life, and are not suitable for continuous wireless transmission for more than 12 hours. In chronic conditions (e.g. autism, sleep disorders, epilepsy, PTSD, bipolar disorder, etc.), there is a need to collect physiological data continuously over weeks and months. Given a typical coin cell battery with a capacity of a few hundred milli-amp hours, this requires that the average power consumption of the wearable system be 1 milliwatt or less. This level of power consumption cannot be achieved by radio design alone; it also requires proper design of the sensing hardware.

Also, existing wireless biosensor devices are generally limited to a single user and do not support data collection from multiple users simultaneously. In addition, another important concern with existing devices is their generally limited data analysis, e.g., simply to record data such as heart rate.

SUMMARY OF THE INVENTION

This invention provides a new approach to sensing and communicating patterns of physiological data without encumbering the participant. A preferred embodiment of the invention takes the form of a washable, wearable biosensor that can wirelessly gather, communicate, and analyze data in real-time as a person goes about their normal lifestyle activities.

The packaging design and materials employed in this invention allow a level of comfort that has not been available with traditional electrodes and adhesives, which cause skin irritation when kept in place for long periods of time (sometimes in hours, but especially a problem when worn for days or weeks, say to gather autonomic circadian rhythms.) The invention provides the ability to wear this device in multiple positions, to slip it up or down the wrist, and to put it on or remove it quickly without having to apply or remove gels and adhesives. At the same time the apparatus provides a snug, comfortable fit and gathers data with minimal motion artifacts, also allowing the data to be combined with information from integrated motion sensors if motion is of concern or interest.

The invention may be used to advantage to implement photoplethysmography. A photoplethysmograph (PPG) is an optically obtained plethysmograph, a volumetric measurement of an organ. A PPG is often obtained by using a pulse oximeter which illuminates the skin and measures changes in light absorption. A conventional pulse oximeter monitors the perfusion of blood to the dermis and subcutaneous tissue of the skin. With each cardiac cycle the heart pumps blood to the periphery. Even though this pressure pulse is somewhat damped by the time it reaches the skin, it is enough to distend the arteries and arterioles in the subcutaneous tissue. If the pulse oximeter is attached without compressing the skin, a pressure pulse can also be seen from the venous plexus, as a small secondary peak. The change in volume caused by the pressure pulse is detected by illuminating the skin with the light from a Light Emitting Diode (LED) and then measuring the amount of light either transmitted or reflected to a photodiode. Each cardiac cycle appears as a peak, as seen in the figure. Because blood flow to the skin can be modulated by multiple other physiological systems, the PPG can also be used to monitor breathing, hypovolemia, etc. The invention also allows integration of photoplethysmography, skin conductance, motion, and temperature in a small wearable package. This invention can be used for cooperative patients. In addition, it can be used with subjects such as infants, young children, adults with dementia or other impairments, and animals.

In some embodiments, this invention employs textile-based wearable form factors (e.g. wrist and palm) made of breathable materials and avoiding hard bulky plastic containers. An important feature of this form factor is that it can be flexibly moved to multiple positions to avoid covering the same area of skin for too long with any non-breathable component.

Embodiments of the invention enable non-traditional electrode placement (wrist, palm, foot) built with removable clothing snaps, aerated (hole-punched) conductive rubber, and other conductive fabric materials that do not require gels. This is important for preventing skin irritation from covering the skin with a non-breathable material for too long. This is also important for making it easy to put on or take off the device in a single step (no need to apply gels or adhesives, or rub these off the skin.)

Also, embodiments of the invention support multiple users, by employing channel-sharing wireless protocols to enable the transmission of data from multiple users and multiple sensors (e.g. both sides of body, wrists or hands and feet, or multiple people). The channel sharing protocols include ad-hoc CSMA (carrier sense multiple access) protocol and time-slotted TDMA (time division multiple access) reader-mediated protocol In some embodiments, this invention includes pattern analysis software. An on-board processor can map patterns of the physiological and motion data to signals or alerts such as a likely seizure, drug craving, or other states that the wearer would like to know about or use to alert other people or devices for assistance. Pattern analysis can also be performed in the device receiving the wireless data.

In addition to a computer device for receiving the data, the present invention may have one or more data output devices used for displaying the data. The wireless transmission can be received by a mobile phone or other personal digital device, a computer, a favorite toy, or another wearable device. For example, a physiological sensor may communicate with a favorite toy that displays the data.

In some embodiments, this invention has two features to improve data integrity. First, it uses multiple PPGs. Combining signals from multiple PPGs using signal processing reduces noise caused by motion artifacts. Second, this invention employs logarithmic detection. This is especially important in small battery powered sensors that have low power rails (0-3V or 0 to 1.8V) and hence small dynamic range and also this is important to be able to better handle the motion artifacts that one encounters in a wrist-worn form factor.

The above summary provides a simplified introduction to some aspects of the invention as a prelude to the more detailed description that is presented later, but is not intended to define or delineate the scope of the invention.

BRIEF DESCRIPTION OF THE DRAWINGS

In the detailed description which follows, frequent reference will be made to the attached drawings, in which.

DETAILED DESCRIPTION

Figure 1:
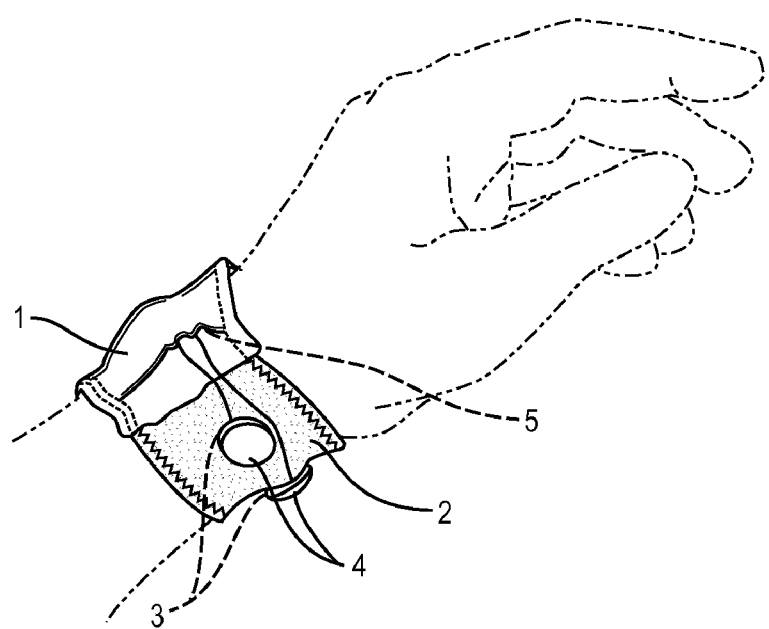
FIG. 1 illustrates a wrist/hand band with an electrodermal activity (EDA) sensor, being worn on the wrist.

FIG. 1 shows a flexible wrist/hand band with a sensor to detect electrodermal activity (EDA), also known as galvanic skin response. In FIG. 1, the band is being worn on the wrist.

The electrodes for the EDA sensor [3] are made of one or more electro-conductive materials, including conductive fabrics and yarns, conductive polymers, conductive elastomers or metal. A variety of these materials are available from commercial sources. For example, the fabric can be a medical-grade silver-plated 92% Nylon 8% Dorlastan fabric (Cat. # A251, Less EMF, Inc., Albany, N.Y.). This electro-conductive fabric is washable, allows the skin to breathe, maintains elasticity and provides consistent contact with the skin.

Alternatively, the electrode comprises electro-conductive thread or yarn embroidered into fabric or other material. For example, a stainless steel electro-conductive thread sold by Bekaert (Winston Salem, N.C.) can be used. This enables greater comfort and durability since the conductive thread exhibits less strain fatigue than traditional metal wires. Alternatively, electrically conducting elastomers or polymers may be used for the electrodes. Poly(3,4-ethylenedioxythiophene), also known as PEDOT, is an example of such a conducting elastomer. Carbon-impregnated rubber is an example of such a conducting polymer. These conductive elastomers and polymers are not generally breathable and thus less desirable. This problem may be solved in some cases by aeration (i.e., hole-punching) that makes the material more breathable. For example, carbonized rubber may be aerated in that fashion. Alternatively, standard medical metal electrodes may be used. For example, silver-silver chloride electrodes (such as those commonly used in electrocardiographs) may be used. These provide good contact with the skin. The metal electrodes are preferably detachably mounted on the fabric using pop-in snaps or the like.

Metal snaps [4] may be used to connect the electrodes (or leads from them) to the circuit (or lead from it). When the snaps are snapped together, the electrodes and circuitry are electrically connected; when they are snapped apart, they are not electrically connected. These snaps thus enable the circuitry to be repeatedly attached to and detached from the wearable band with electrodes. The wearable band with electrodes can then be easily washed or replaced. The placement of the metal snaps [4] may vary. For example, the snaps may be near the electrodes, or near the circuitry instead. Alternatively, other electrical connectors may be used instead of the metal snaps. In some implementations, the electrical connector will be light-weight and at least one part of the connector will be washable.

The circuitry for the EDA sensor [5] fits, and is secured, within a hydrophobic pouch on the band. This protects the circuitry from contact with the wearer, liquids or other external objects.

A hydrophobic, breathable material [1] is used to form the pouch for circuitry, and to form parts of the wearable band. In some embodiments, this material is Gore-Tex. In some other embodiments, Dryline fabric (from Milliken & Company) is used. This stretchable fabric is hydrophilic on the inner layer and hydrophobic on the outer layer, so that moisture moves away from the wearer's skin through the fabric to the outer layer, where it evaporates. Alternatively, other hydrophobic, breathable materials may be used. For example, eVent fabric (sold by BHA Group, Inc., Kansas City, Mo.) or Epic fabric (sold by Nextec Applications, Inc., Bonsall, Calif.) may be utilized. Fabrics comprising a mix of elastic and leather may also be used to advantage.

The electrodes are hosted by a flexible, breathable material [2]. A wide range of these materials are available commercially. In some embodiments, a synthetic stretch mesh, such as 85% nylon and 15% Lycra blend, is used. In some embodiments, the material used in [2] may be the same as the breathable, hydrophobic material used in [1].

A flexible closure [6] is used to fasten the two ends of the band together. In some embodiments, the flexible closure comprises Velcro strips and a metal snap fastener.

The wrist is not a standard location for measuring EDA since the sweat glands there tend to be less sensitive than those on the palm or fingers, where EDA is traditionally measured. This issue, coupled with the use of dry electrodes in some embodiments, means that it usually takes at least 15 minutes (depending on humidity and the individual's temperature) before the moisture buildup between the skin and electrodes is sufficient to show a range of responsiveness on the wrist. The main advantage of sensing EDA from the wrist is that the sensor can be comfortably worn for long periods of time (days and weeks) by adults and by small children (ages 3-6) without interfering with daily activities, such as sleeping, washing hands, or typing. If desired, the wrist-worn strap can be slid up onto the palm for a more sensitive EDA response.

Figure 2:
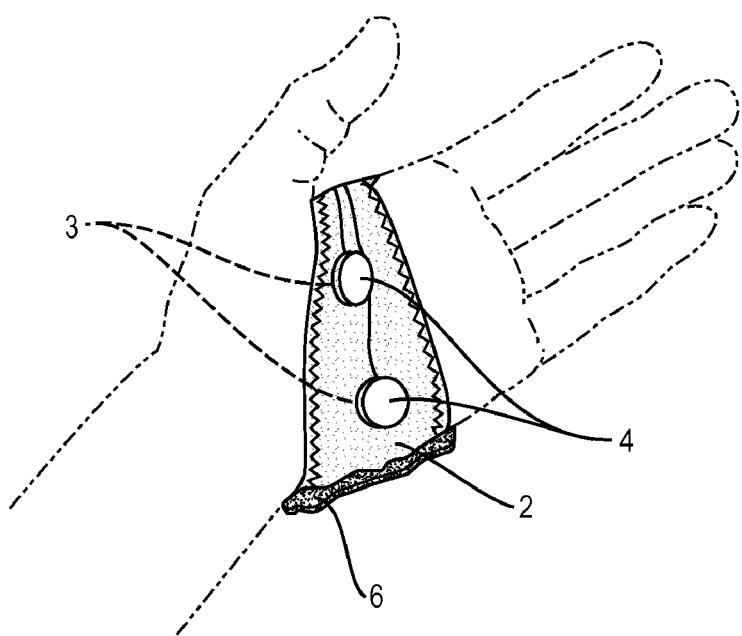
FIG. 2 illustrates the same band, being worn on the hand/palm.

FIG. 2 illustrates the same wearable band with EDA sensor as that in FIG. 1. However, in FIG. 1, the band is being worn on the wrist; whereas in FIG. 2, it is being worn on the hand/palm.

Figure 3:
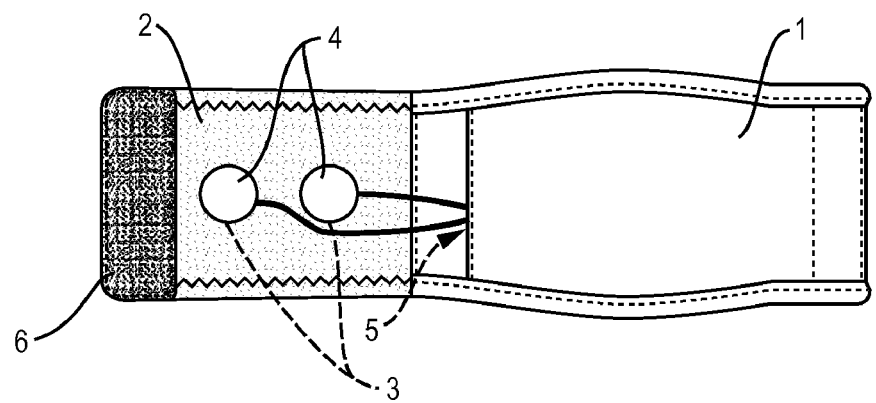
FIG. 3 is a plan view of the outer side of the same band.

FIG. 3 is a planar view of the exterior of the same band.

Figure 4A:
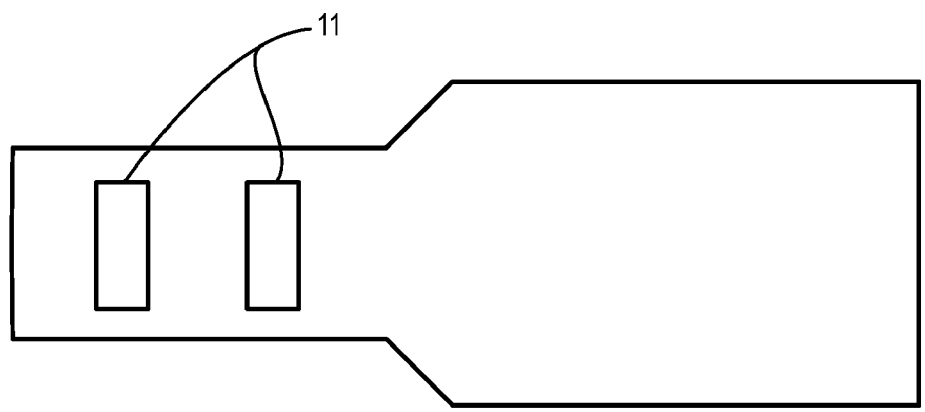
FIG. 4 is a plan view of the inner side of a wrist band, showing two examples of placement of electrodes for an EDA sensor.
Figure 4B:
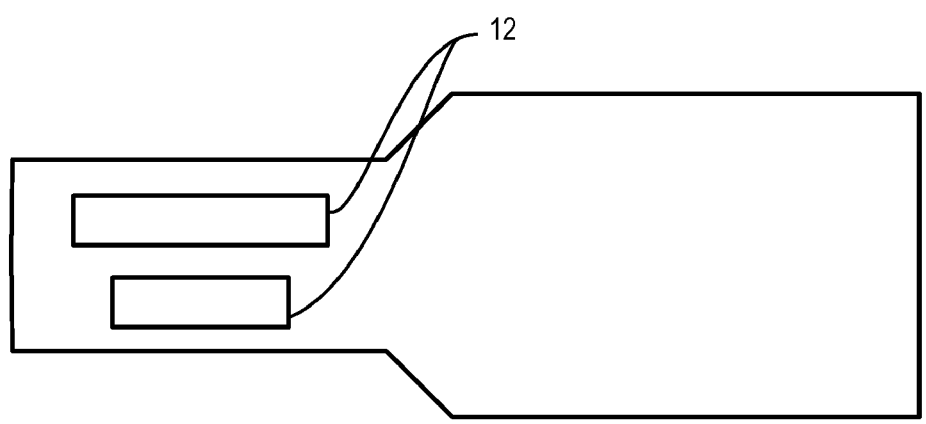

FIG. 4 is a planar view of the interior of a band that may be worn on the wrist or palm. It shows alternate examples of the position of electrodes [11] and [12].

Figure 5:
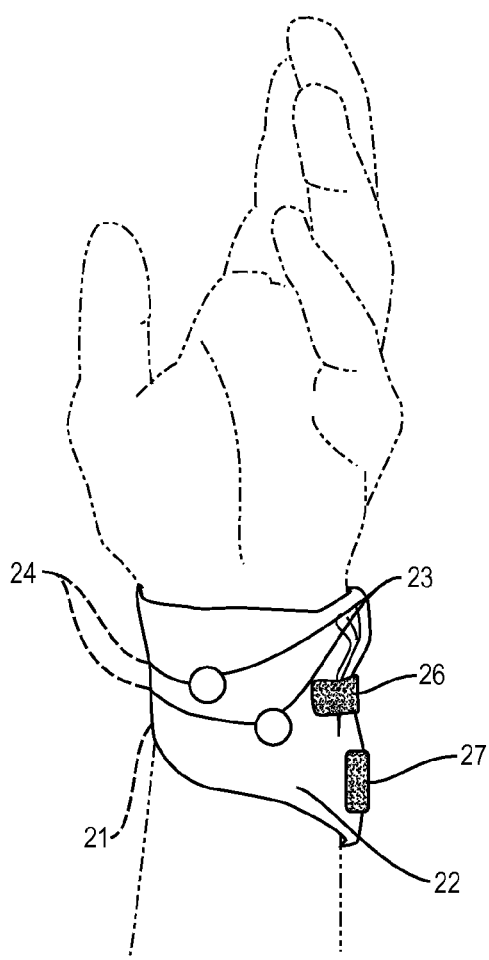
FIG. 5 illustrates a wrist/thumb band, being worn with thumb not inserted through thumbhole.
Figure 6:
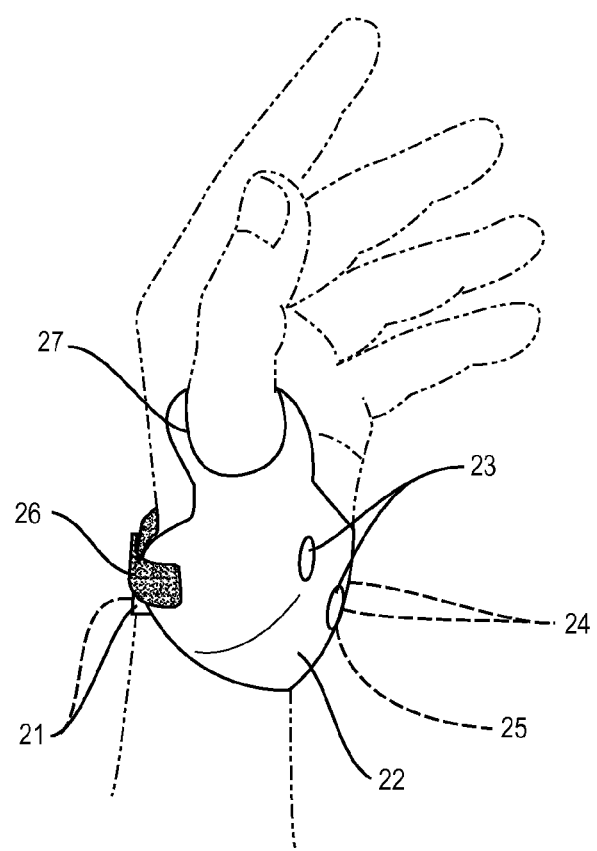
FIG. 6 illustrates a wrist/thumb band, being worn with thumb inserted through thumbhole.

FIG. 5 and FIG. 6 illustrate an embodiment in which the wearable band has a thumbhole [27]. The band may be worn with the electrodes [23] on the palm and the thumb inserted through the thumbhole [27], as shown in FIG. 6. Or it may be worn with the electrodes [23] on the wrist and the thumb not inserted through the thumbhole [27], as shown in FIG. 5.

In many respects, the embodiment shown in FIG. 5 and FIG. 6 (the wrist/thumb band) is similar to that shown in FIG. 1 and FIG. 2. The electrodes [3 and 23], hydrophobic, breathable material [1 and 21], flexible, breathable material [2 and 22]) and flexible closure [6 and 26]) can be made of the same materials in both of those bands.

Likewise, the metal snaps or other electrical connectors [4 and 24] function in a similar manner in both bands.

Figure 7:
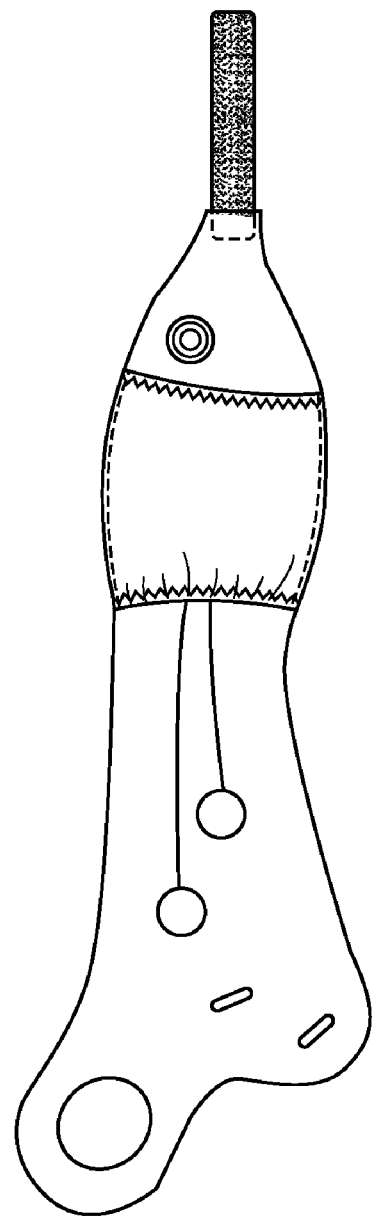
FIG. 7 is a plan view of the outer side of a wrist/thumb band with a thumbhole.

FIG. 7 is a planar view of the exterior of the same wrist/thumb band with a thumbhole.

Figure 17:
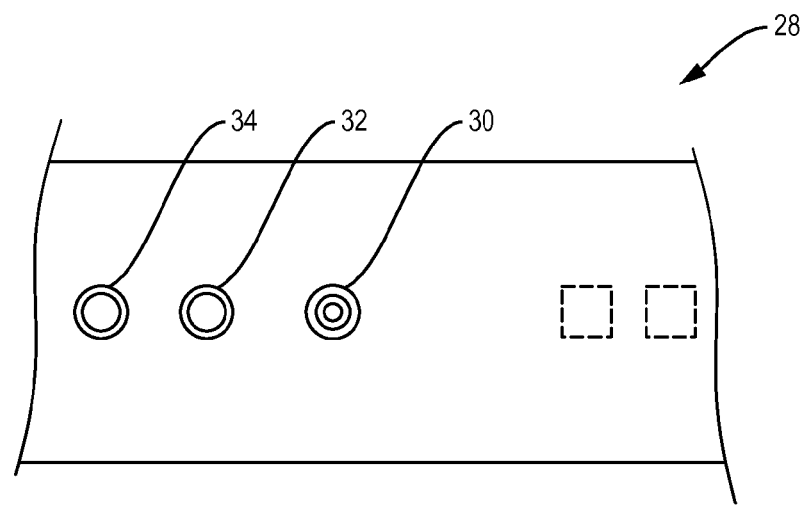
FIGS. 17-19 show the construction of an adjustable wristband for supporting one or more sensors on the wrist or palm.
Figure 18:
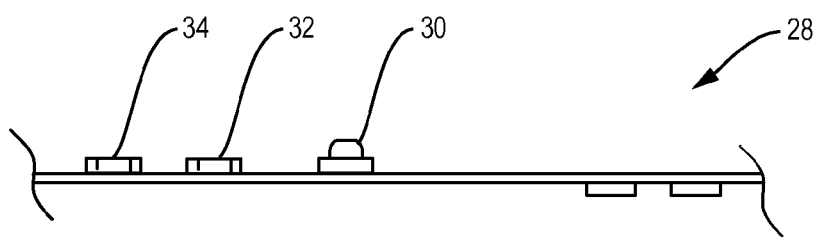
Figure 19:
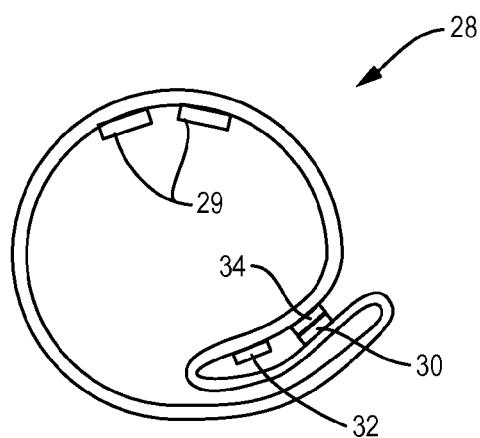

FIGS. 17 and 18 show plan and edge views respectively of an alternative adjustable wrist band [28] which mounts electrodes [3]. The ends of the fabric forming the wristband are joined to form a loop as seen in FIG. 19. The circumference of the wrist band may be adjusted by snapping the male fastener [30] to either the near female fastener [32] or the more distant female fastener [34] as seen in FIG. 19. The three snap fasteners are sewn into the wristband fabric. The smaller circumference may be used when the wristband is being worn by a child. More than two female snaps may be employed to provide greater adjustability. The arrangement seen in FIGS. 17-19 provides a snug fit that properly positions the electrodes against the patient's wrist.

Figure 8:
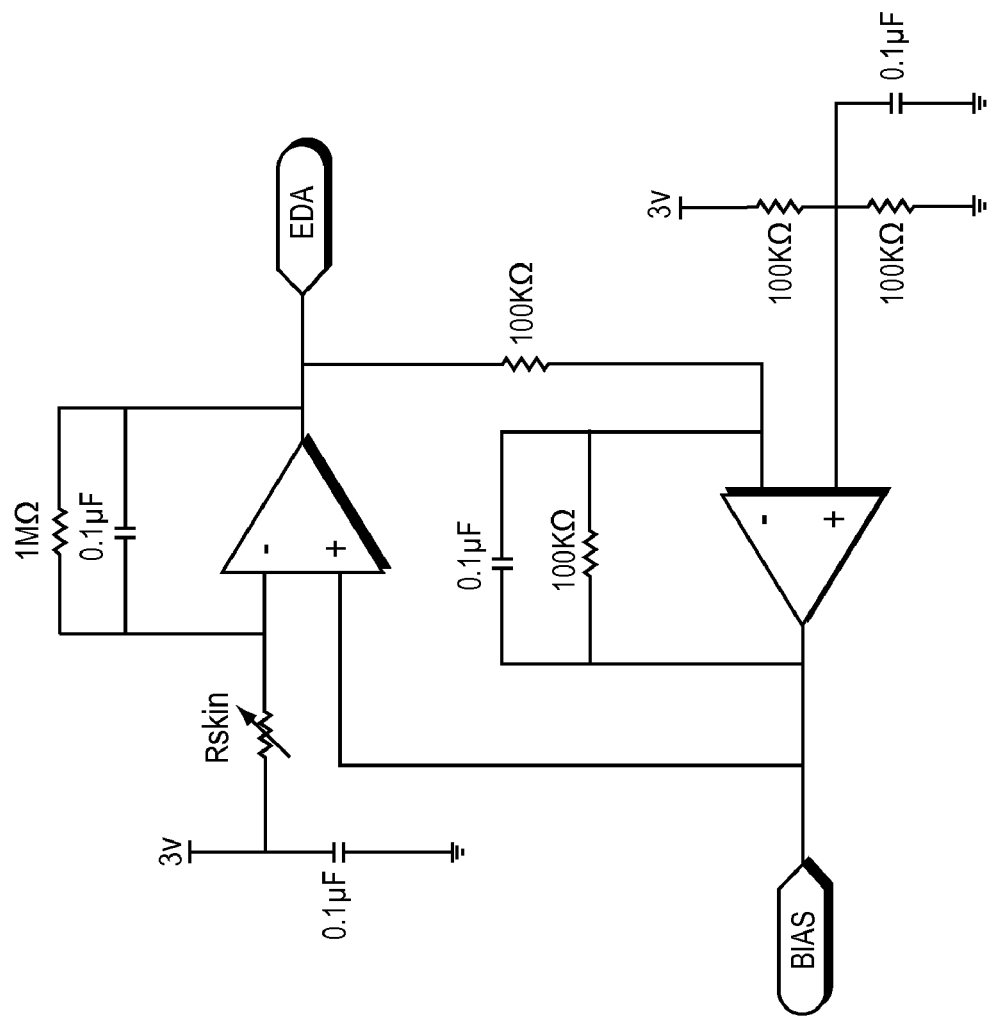
FIG. 8 is a schematic of a circuit used to measure electrodermal activity (EDA).

FIG. 8 is a schematic of an illustrative embodiment of the circuit used to measure electrodermal activity (EDA). The EDA sensor module implements an exosomatic measurement of EDA, such that a small voltage is applied to the skin and the resulting potential drop is measured. The primary technical challenge in creating this circuit was to achieve a low-power design while still maintaining good dynamic range. It is well known that baseline skin resistance can vary over a few orders of magnitude from 100 KOhms to approximately 10 MOhms; yet, it is necessary to detect minute changes in this value. Greater dynamic range and sensitivity could be achieved by increasing the voltage rails. However, in this embodiment, 3 Volts is chosen for the positive voltage rail in order to minimize power consumption and enable interfacing to low-power radios.

Another approach to maximizing dynamic range is to use a digitally controlled variable gain amplifier. However, this requires the use of an external microcontroller that adds greater cost, complexity, and power consumption.

As shown in FIG. 8, the EDA circuit in some instantiations includes an op-amp circuit with non-linear feedback that automatically scales gain to compensate for the large range in skin conductance. In some versions, using an op-amp with a low-leakage current (such as the AD8606, Analog Devices, Inc., Norwood, Mass.), the invention achieves a measurement circuit with wide dynamic range and low power consumption (<1 mA at 3V). Other approaches can also be used to address the need for large dynamic range, including transistors or diodes in the op-amp feedback circuit or using a digitally-controlled programmable gain amplifier.

In some embodiments, the EDA performs a time-domain measurement of skin conductance by employing an oscillator circuit whose oscillation frequency is dependent on the skin conductance. By measuring this frequency instead of measuring the skin resistance directly, it is possible to perform a more precise measurement given the low power rails and limited dynamic range of the voltage.

In order to maximize battery life and maintain a stable voltage rail for the op-amps and sensors, a low-power low-noise regulator is added in some embodiments (LM1962, National Semiconductor, Santa Clara, Calif.). This regulator has a power enable pin that can be used to only momentarily provide power sensor module and power it off when it is not in use, thereby reducing the power consumption of the entire EDA sensor module to less than 20 microwatts.

Figure 9A:
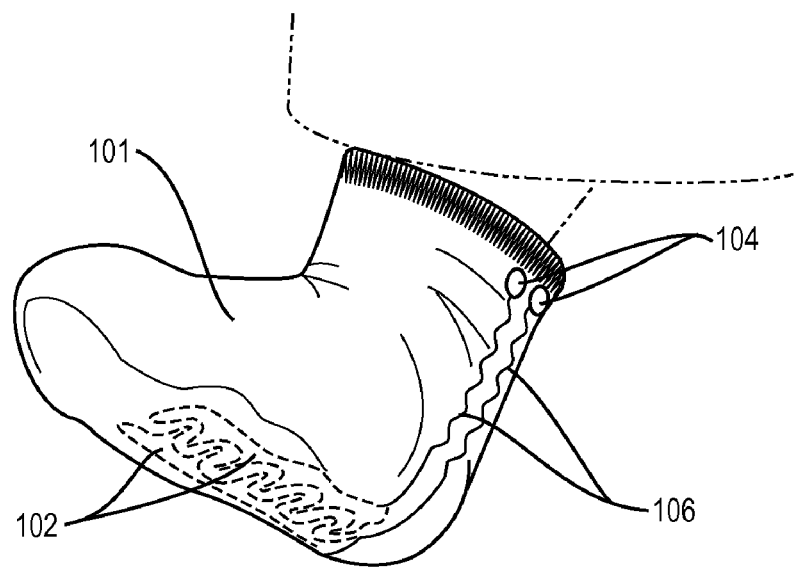
FIG. 9 illustrates a sensor module with electrode leads in a sock and circuitry in a shoe.
Figure 9B:
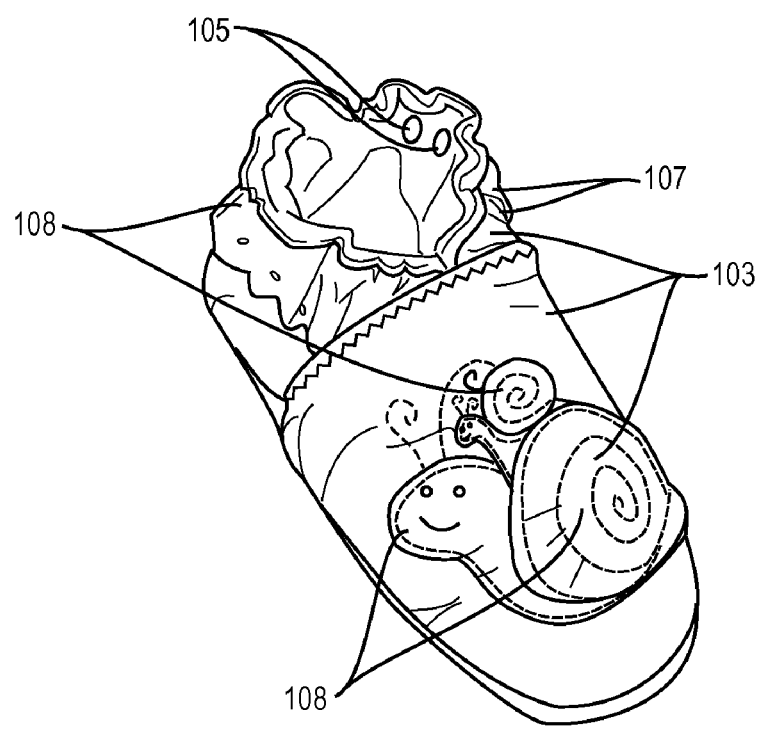

FIG. 9 shows a version that can be worn on the feet of newborn infants (whose hands and wrists are often in their mouths, and thus undesirable for sensing). The sole of the foot has eccrine sweat glands like the palm of the hand, and this site provides a more traditional measurement of EDA. In this embodiment, soft electrodes [102] are sewn into or printed on the socks and attached via small magnetic clothing snaps [104 and 105] to the sensor circuitry [108] which is safely sealed into the top of the shoe so the infant cannot get to the small parts. Leads [106 and 107] from the electrodes to the circuitry are flexible and insulated from contact.

In many respects, the embodiment shown in FIG. 9 (the shoe/sock package) is similar to the embodiment shown in FIG. 1 and FIG. 2. The electrodes [3 and 102], hydrophobic, breathable material [1 and 103], and flexible, breathable material [2 and 101] and flexible closure [6 and 26] can be made of the same materials in both embodiments.

Likewise, the small magnetic clothing snaps [104 and 105] in FIG. 9 function in a similar manner to the metal snaps [4]

in FIG. 1 providing electrical contact to the measurement electronics. The snaps [104 and 105] can be attached and reattached, allowing removal of socks with electrodes from the shoes. The socks can then be easily washed or replaced.

Sensor circuitry for a plurality of sensors [108] are contained and secured in insulated pocket sections of the shoe under appliqués and trim. This helps protect the circuitry from contact with persons, liquids or other external objects.

In some embodiments, the infant shoe/sock package includes EDA, temperature, and motion sensors. Alternatively, the separate shoe/sock package can be implemented in a size and shape suited for older patients. For example, such a sock/shoe implementation can be used for an older patient with dementia, who might not cooperate with a wrist band. In some embodiments, the invention may be used with animals.

Figure 10:
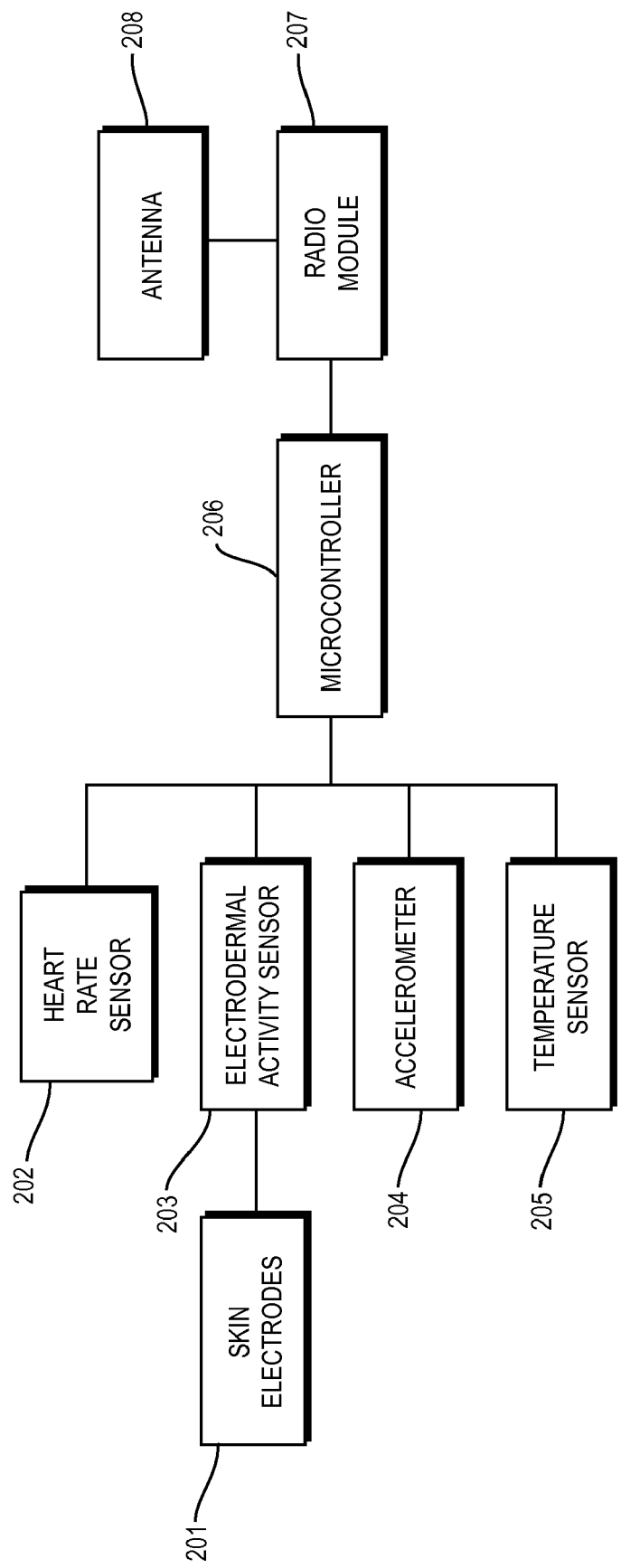
FIG. 10 is a block diagram of a wearable biosensor that comprises a plurality of sensors, microprocessor, radio module and antenna.

FIG. 10 is block diagram that shows how, in some embodiments, the wearable biosensor has more than one sensor [202, 203, 204 and 205]. The wearable biosensor also includes a microcontroller that processes data from the sensors [206], a radio module [207] and antenna [208]. The radio module and antenna are used solely for transmission in some embodiments and operate as a transceiver in other embodiments. The plurality of sensors may include an EDA sensor [203], a heart rate sensor [202], accelerometer [204] and temperature sensor [205]. Electrodes [201] for the EDA sensor are included.

In some embodiments, the wearable biosensor includes at least one photoplethysmograph (PPG). The PPG may be used for measuring heart rate (HR) and heart rate variability (HRV). Since the light absorption of blood is wavelength dependent, if two different wavelength LEDs are used, then it is also possible to measure the relative blood oxygen level using the ratio of readings between the two color LED's.

Figure 11:
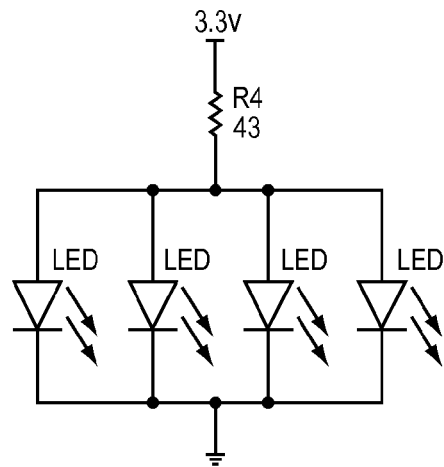
FIG. 11 is a circuit schematic for a linear strip of LEDs, that is part of a photoplethysmograph (PPG) heart rate sensor.
Figure 12:
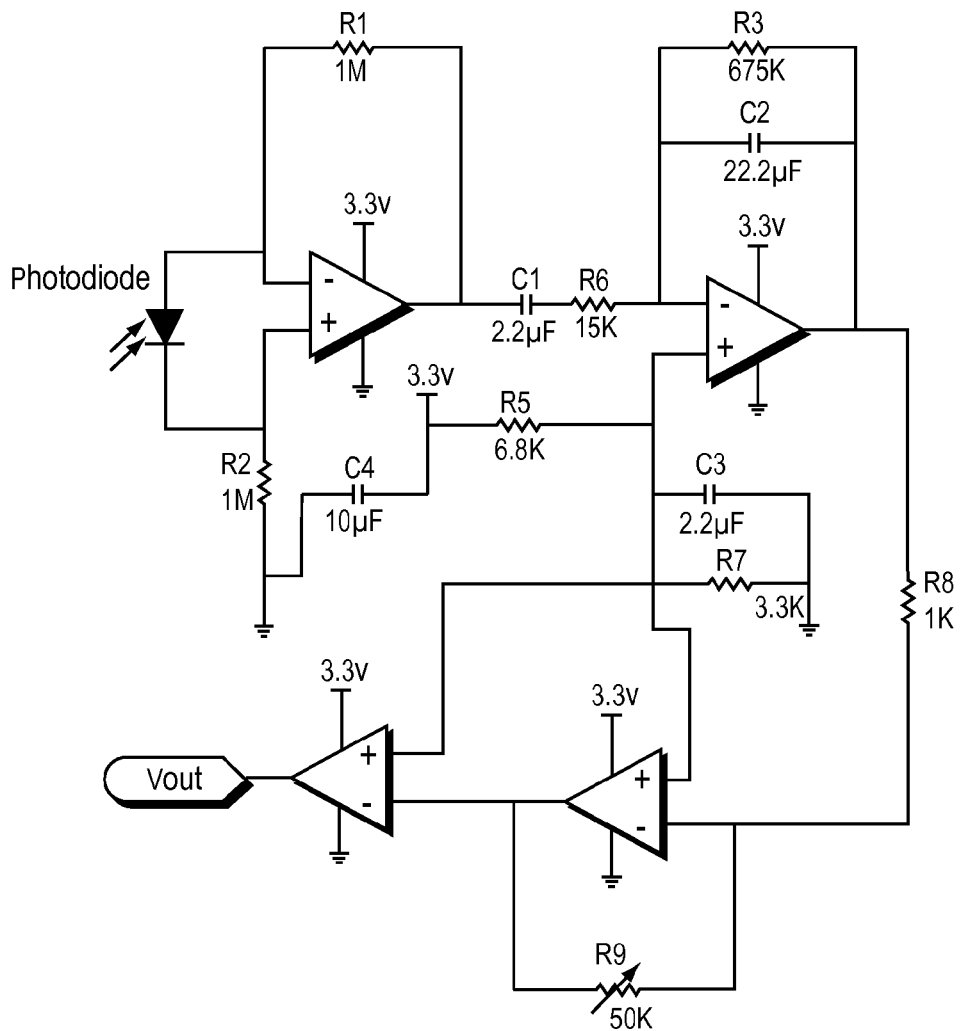
FIG. 12 is a circuit schematic for PPG heart rate sensor, including photodiode.

While commonly available PPG devices employ a single LED light, FIG. 11 depicts an illustrative embodiment of the present invention which uses multiple LEDs. Because of the wearable nature of the device, multiple LEDs are used in order to minimize noise and error due to motion, inexact placement, and slippage of the wristband over the blood vessels. In some embodiments, the photodiode absorbs light reflected from the skin. In other embodiments, the photodiode absorbs light transmitted through tissue. FIG. 12 is a schematic of an illustrative embodiment of the photodiode and PPG sensor circuit. This implementation is designed to be low-power and low-cost. As such, a rail-to-rail operational amplifier with a high slew rate, a low input bias current ($I_{IB}$), a low minimum operating voltage, a gain bandwidth higher than 0.9, an Iq less than 1 mA, and a low price is desired. In some versions, the TLV2784 (Texas Instruments, Dallas, Tex.) is used as the operational amplifier in the PPG sensor because it meets all of the aforementioned requirements: rail-to-rail input and output, a minimum operating voltage of 1.6 V, a high slew rate of 4.3 V/uS, $I_{IB}$ of 15 pA, Iq of 0.82 mA per channel, a gain bandwidth of 8 MHz, and a low price. The PPG sensor's output signal varies with respect to blood volume and consists of two peaks, both of which are nameless. The large, periodic peaks present in a PPG signal lag behind the R wave (of the QRS wave complex of an electrocardiogram), occur at the same frequency as R waves and can therefore be used for calculating heart rate, heart rate variability (HRV) or vagal tone For ease of description in the remainder of this description of the invention, the main (large, periodic) peak in a PPG will be referred to as R wave. The smaller, secondary peaks in a PPG wave correspond to venous pulsations. The following describes an illustrative embodiment of the PPG circuit, with four stages.

As shown in FIG. 12, the first stage of the circuit is a transimpedance amplifier, which converts the current produced by the photodiode into voltage. A 1 MΩ resistor is placed at the positive input of the op-amp because it doubles the value of the input signal without doubling the gain.

The second stage is a bandpass filter with corner frequencies 4.8 Hz and 10.6 Hz, a bias voltage of 1.08 V, and a gain of 45. The low cutoff value was chosen because it eliminated the DC bias and removed baseline frequencies without deforming the QRS complex of the heart beat. Since this is only a first order filter, the high cutoff value was chosen at 10 Hz to ensure the elimination of 60 Hz noise. This simple RC first order filter was implemented instead of more complicated higher order filters to minimize the noise introduced by additional stages. Since within the QRS complex, the R wave has higher amplitude than both the Q and S segments, the bias voltage was set a bit lower than 1.65 V, which is half of $V_{cc}$, to prevent signal saturation.

The signal obtained via PPG on the wrist has very small amplitude; therefore, a high gain is necessary in order to place the sensor's output signal within the proper range so that the microcontroller can detect the R wave peaks. The value of this gain, however, varies from user to user. For instance, a male adult with thicker skin will need a higher gain than a child with small wrists. A 50 KΩ wheel potentiometer was placed in the third stage of the PPG heart rate sensor in order to enable users to adjust the gain so that the signal falls within the proper range. A wheel potentiometer, as opposed to a rotary potentiometer or a rheostat, was chosen so that the user would be able to easily adjust the gain without the use of a screw driver or similar tools.

The fourth stage of the PPG heart rate sensor is a buffer with a bias of 3.3 V. Since the output of the third stage is an inverted heart beat signal, the sole purpose of the buffer is to invert the signal so that the output of the overall circuit properly represents a heart beat signal. It is essential that the output has the correct polarity so that the comparator in the microcontroller can properly detect the R wave peaks. The output of the heart rate sensor is then connected to an 8-bit microcontroller, specifically the Atmel ATmega 168 (Atmel Corporation, San Jose, Calif.), which detects the R wave peaks in the signal. It operates very similarly to a comparator: when the input signal is higher than 1.5 V, it counts it as beat and ignores the signal as it decreases back to its baseline value. As the R wave reoccurs, the signal increases yet again. As it crosses the 1.5 V threshold, the microcontroller records another beat. It then subtracts the two obtained time stamps to determine the time between the two R waves. Next, the time difference values between ten consecutive R waves are averaged and used to calculate the user's heart rate. As such, in this illustrative embodiment, it is preferable to adjust the gain in the third stage of the circuit to a value such that the R wave peak crosses the 1.5 V threshold level. Preferably, the gain is not set too high, so that the amplitude of the input signal's other components remains below 1.5 V. For instance, if the gain is too high, then (a) the R wave could be saturated at 3.3 V while the smaller, secondary PPG waveform also crosses the 1.5 V threshold, and (b) the microcontroller, in turn, could count both waveforms in determining the user's heart rate and could produce a heart rate value that is too high.

Alternately, the EDA sensor circuit, PPG sensor circuits and LED circuit could be designed in other ways than the implementations described above.

In some embodiments, one or more motion sensors are included. In some embodiments, an analog motion sensor (SQ-SEN-200, Signal Quest, Lebanon, N.H.) with an integrator circuit is used. The advantage of this analog sensor, over a 3-axis accelerometer, is that it draws less than 1 microamp of current and is inexpensive to purchase.

Alternatively, various types of motion sensors may be used, including 3 axis digital accelerometers. For example, the motion sensor may be any of various types of micro electro-mechanical systems (MEMS) consisting essentially of a proof mass on a damped spring, that measure the deflection of the proof mass in an analog or digital manner. For example, the deflection may be measured by piezoresistors attached to the spring, or by changes in capacitance between fixed beams and beams attached to the proof mass. Also, for example, the accelerometer may have a small heated dome of gas and measure the deflection of the center of the dome.

A motion sensor can also be used to gate the PPG signal so that heart rate data during motion can be ignored or cleaned. It should be noted, however, that there are many times during the day or night when a person's wrists are still, thus allowing for snapshots of HR and HRV. The combination of motion, EDA and HR/HRV are particularly relevant for recognizing sleep stages and conditions such as apnea. In some embodiments, multiple PPG sensors are employed. The multiple PPG signals are combined using signal processing, which reduces noise caused by motion artifacts. In some versions of the invention, logarithmic detection is used, which also helps handle motion artifacts.

The wearable biosensor may include a temperature sensor. In some implementations, a low-power temperature sensor (LM60, National Semiconductor, Santa Clara, Calif.) is used.

In some embodiments, one or more PPG heart rate sensors, motion sensors and temperature sensors are removable in their entirety from the wearable biosensor, so that they can be easily removed or replaced, for example, when the band or other host material for the sensor is washed. In other embodiments, one or more of these sensors are coated in plastic or another waterproof or water-resistant material, so that they can remain with the wrist band (or other wearable garment or material) when it is washed. In the case of PPG sensors, this coating is preferably transparent to the wavelength of light (including red or infrared light) emitted by the LEDs and absorbed by the photodiode. In the case of any temperature sensor, this coating preferably has a high thermal conductivity. In versions where these sensors remain with a band (or other wearable garment or material) when it is washed, leads may be used to connect the sensors with the removable circuitry, including the radio module and antenna. Metal snaps or other electrical connectors are used to enable the sensors (or leads from them) to be repeatedly attached to or detached from the removable circuitry (or leads from it).

In some embodiments, rechargeable batteries are used. This not only eliminates the need to purchase hundreds of batteries that may be needed for long-term use, but enables the battery to be completely embedded inside the wearable package for weatherproofing and safety reasons (e.g., for infant use).

In some implementations, the invention includes a radio module and antenna. In some versions of the invention, the wireless network enables wireless data collection and easy sharing and access to the physiological data across a variety of devices, including personal computers, PDAs, mobile phones, and the Internet. In addition, in some versions, the wireless network supports data collection from multiple (e.g. dozens) radio modules simultaneously. In some cases, the radio module is designed to minimize size and maximize battery life.

Many radio protocols and open standards are now available; however, most do not support multiple sensors and are not compatible with low-power radio hardware. For this reason, some embodiments of the invention employ IEEE 802.15.4, which in recent years has emerged as the dominant wireless protocol for low-power sensor networks, and is also the physical-layer protocol for Zigbee. Alternatively, the Ultra-WideBand standard IEEE 802.15.4a could be used. Although higher-level transport protocols such as Zigbee support multi-hop routing and mesh networking, some implementations of the invention adopt a star topology for the network in order to minimize processing overhead and power consumption. This radio hardware also provides a wireless operating range of 25 meters.

Many wireless sensors operate in the UHF range, e.g. 433 MHz, 915 MHz. Some embodiments of the invention, however, operate with 2.4 GHz in order to enable a smaller antenna size and achieve better indoor radio propagation.

There is a practical need to set the ID code of each radio module and to configure the transmission or sampling rate of each module. In some embodiments, to meet these needs, a command protocol is added using a "command and response" paradigm. The following is an illustration of how such a command protocol operates: To send a command to a specific radio module, the command is first sent to the radio base station. The command is stored in the base station "command queue" until the specific radio module wakes up and transmits its data packet to the reader (base station). The command is then transmitted to the specific radio module, which receives the command and immediately executes it before going back to sleep.

In some embodiments, the radio module comprises an Atmega168V microcontroller (Atmel Corporation, San Jose, Calif.) and a Chipcon CC2420 RF transceiver (Texas Instruments, Dallas, Tex.). In some versions, the radio module exposes six 10-bit A/D ports on the microcontroller for interfacing with the sensor module. The reference voltage on these inputs can be configured via wireless commands from the radio base station. In some embodiments, an on-board processor can map patterns of the physiological and motion data to signals or alerts such as a likely seizure, drug craving, or other states that the wearer would like to know about or use to alert other people or devices for assistance. Alternatively, pattern analysis can be performed in the device receiving the wireless data.

In some embodiments, the IEEE802.15.4 protocol is implemented in firmware with independent sampling and transmission intervals that can be set via wireless commands from the base station. Every transmission cycle, the radio module wakes up and then in turn activates the power enable pin on the sensor module to power up the sensors. After a 10 ms delay, the radio module captures a 10-bit A/D sample from each of the sensors, transmits the data packet to the base station, and then goes back to sleep. In some embodiments, data samples from sensors are stored in a cache or buffer before being transmitted.

In some implementations, to reduce cost and provide omni-directional performance, the invention has an integrated printed circuit board antenna. For example, some embodiments employ a bent-dipole, horseshoe-shaped antenna that results in a compact design having a nearly isotropic radiation pattern.

IEEE 802.15.4 communication hardware supports a 250 kbps data rate. However, since EDA data has a relatively low rate of change, it is desirable in some implementations to use a slow sampling rate of 2 Hz and packetized data transmission to enable a very low operational duty cycle and long battery life.

For applications that monitor data from multiple radio modules (e.g. on both left and right wrists), it is necessary to synchronize time between sensors. In some embodiments, the ad-hoc asynchronous nature of the network does not automatically provide a common time base, and to solve this problem, the radio base station is programmed to time stamp each arriving data packet in order to generate a proper time base of the measurements.

In some implementations, the invention employs channel-sharing wireless protocols to enable the transmission of data from multiple users and multiple sensors (e.g., both sides of the body, wrists or hands and feet, or multiple people). As part of the firmware implementation of the IEEE 802.15.4 MAC (Media Access Channel) Layer, the some versions of the invention implement the CSMA (Carrier Sense Multiple Access) algorithm. This algorithm provides exponential back-off in the case of colliding transmissions between two or more radio modules. Different types of the CSMA protocol may be used in the invention, including 1-persistent, p-persistent and non-persistent CSMA. Alternatively, other contention network protocols may be used. For example, any of the following protocols may be used to avoid or reduce data collisions in the wireless network: TDMA (time division multiple access), slotted ALOHA, reservation ALOHA, OFDMA (orthogonal frequency-division multiple access), and MACA (multiple access with collision avoidance).

The CC2420 radio IC has a maximum transmission power of 1 milliwatt (0 dBm), which provides a wireless detection range of 50-75 meters in free space using a 5 dBi gain receiver antenna. Indoor range is significantly less and depends on the building layout, but is approximately 15-20 meters for the module with integrated antenna and 5-10 meters for the version with external antenna. These wireless operating distances are sufficient for many embodiments of the inventions. The radio module also has controllable output power, so the operating distance can be reduced to less than 1 meter as one of several ways to address data privacy. Alternatively, radio modules may employ one or more ICs other than the CC2420.

Privacy and data security are important concerns in many applications of the invention. In addition to controlling the radio output power, the CC2420 radio IC includes hardware support for 128-bit AES encryption, which can be turned on as an option. In some embodiments, the wrist version of our sensor devices also contains a user controlled ON/OFF switch so the user can choose to turn off the data transmission when desired.

In the invention, different types of radio base stations or readers may be used to collect data from multiple radio modules and sensors. For example, the base station can be the ZR-USB, which has a USB interface to plug into PC's and laptops. This base station may comprise the Atmega168V microcontroller, CC2420 radio IC, and the FTDI232BQ USB interface chip (Future Technology Devices International, Ltd., Glasgow, United Kingdom). In some implementations, a 50-Ohm antenna port permits a variety of commercially available 2.4 GHz antennas to be used.

Alternatively, to enable applications that require sending physiological data to a remote web site without a PC, the invention includes a base station using an embedded Linux computer that is programmed to upload data automatically to a remote web server, and is capable of running application-specific programs.

Figure 13:
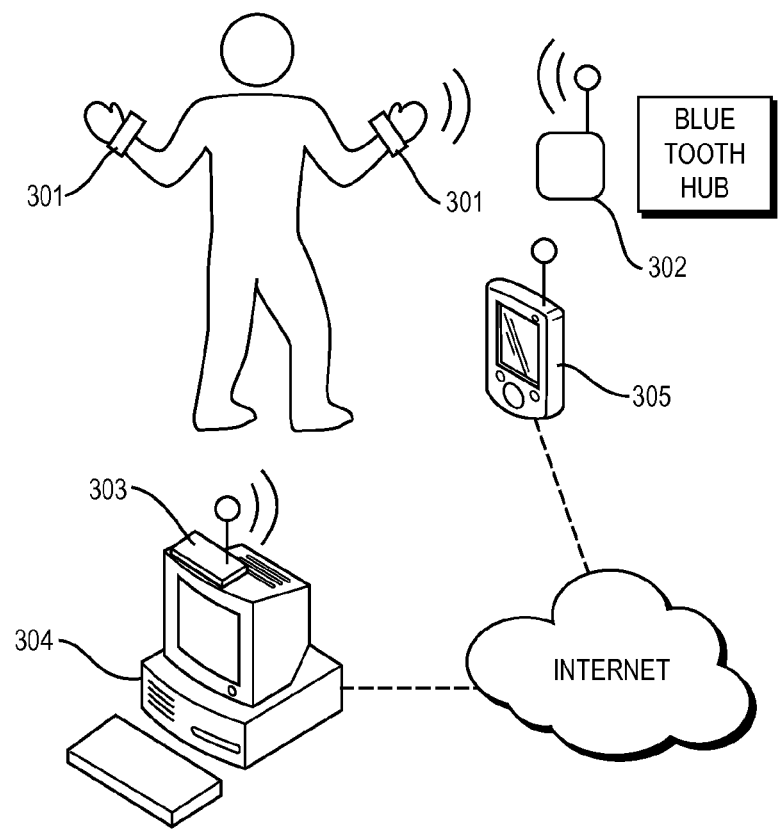
FIG. 13 is a block diagram that illustrates the operation of a wireless network with Bluetooth gateway, that can transmit signals reflective of data obtained from one or more sensors.
Figure 14:
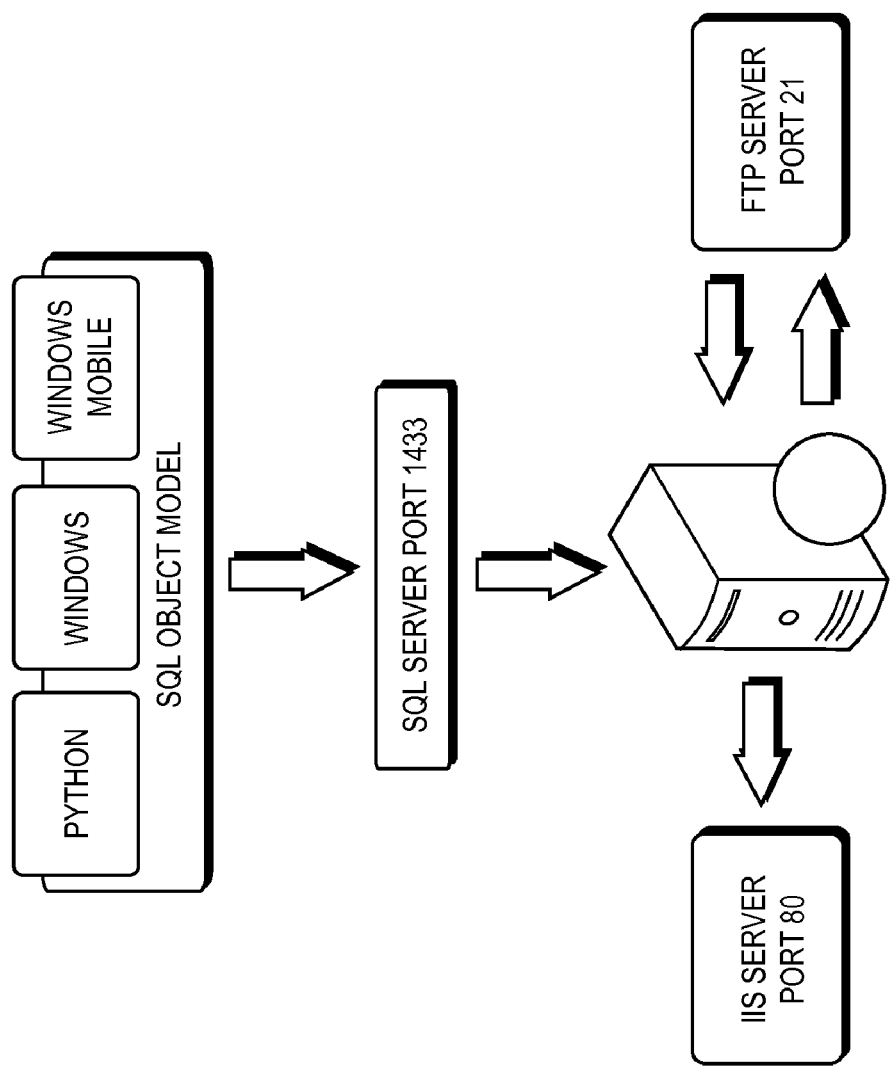
FIG. 14 is a block diagram that shows the server architecture for a website.

For certain applications, it is helpful to receive and display physiological data directly on a mobile phone. Thus, some embodiments of the invention employ a Bluetooth gateway that contains two radios (BlueTooth and IEEE 802.15.4) and is capable of bridging an IEEE 802.15.4 network and Bluetooth network. For example, this gateway can be powered by a rechargeable battery and can contain a Micro-SD card slot for expandable data storage. FIG. 13 illustrates the wireless network architecture that is employed, in some embodiments, for communication between one or more radio modules [301], one or more Bluetooth gateways [302], one or more base stations [303], one or more personal computers [304], and one or more one or more mobile phones [305]. Different versions of the Bluetooth protocol may be used in the invention, including: Bluetooth v1.2 (published as IEEE 802.15.1-2005), Bluetooth v2.0 and Bluetooth v2.1. The sensor data may accordingly be transmitted via a short range Bluetooth network to a cellular phone, and relayed via the cellular network or the Internet to a remote utilization system, which may be implemented by a personal computer, a PDA, an e-book, a music player, a netbook, a gaming system, an interactive exercise system, or any other instrumentality which may be used to present the sensor data, or data derived from the sensor data, in a useful and convenient form to a user. The sensor data may also be advantageously displayed by an ambient display, such as the display devices available from Ambient Devices Inc. described in U.S. Application Publication No. 2003/0076369, the disclosure of which is incorporated herein by reference. In some embodiments, a web site stores, analyzes, and shares collected data. An illustrative server architecture for this web site is shown in FIG. 14.

Alternatively, the web site runs ASP .net (on IIS Server) and draws data from an MSSQL (Microsoft Structured Query Language) database backend. Clients enter data into tables in a parsed format via an SQL Object Model, greatly reducing client-side table row insert errors and server load. This data is dynamically read by an ASP .net client via asynchronous post-backs to deliver database content to end-users. Because data transfer from front end to backend is asynchronous, live data can be read quickly and updated in near-real time. The Microsoft .NET Framework is a component of the Windows operating system. It provides the foundation for next-generation applications, including ASP .NET web applications. The current version of the Microsoft .NET Framework (Version 3.5 SP1) is available for download from Microsoft Corporation at http://www.asp.net. Developers may use the Visual Web Developer 2008 Express Edition, a free development platform also available from Microsoft Corporation at http://www.asp.net, to create ASP .NET web sites.

The web site has a front end ASP .net client that both manages the web server and to act as a client itself. The key feature of the web client is that all data inserted into the MSSQL databases is available in real-time and in graphical form to data consumers. Users may select and view both current and previously recorded files from the database and see if any other users are sharing public data on the server. Additionally, the web site client allows users to filter through archived or live data by turning off data channels viewed on the graphical display. This is particularly useful for analyzing data from a specific channel (i.e. acceleration).

Figure 15A:
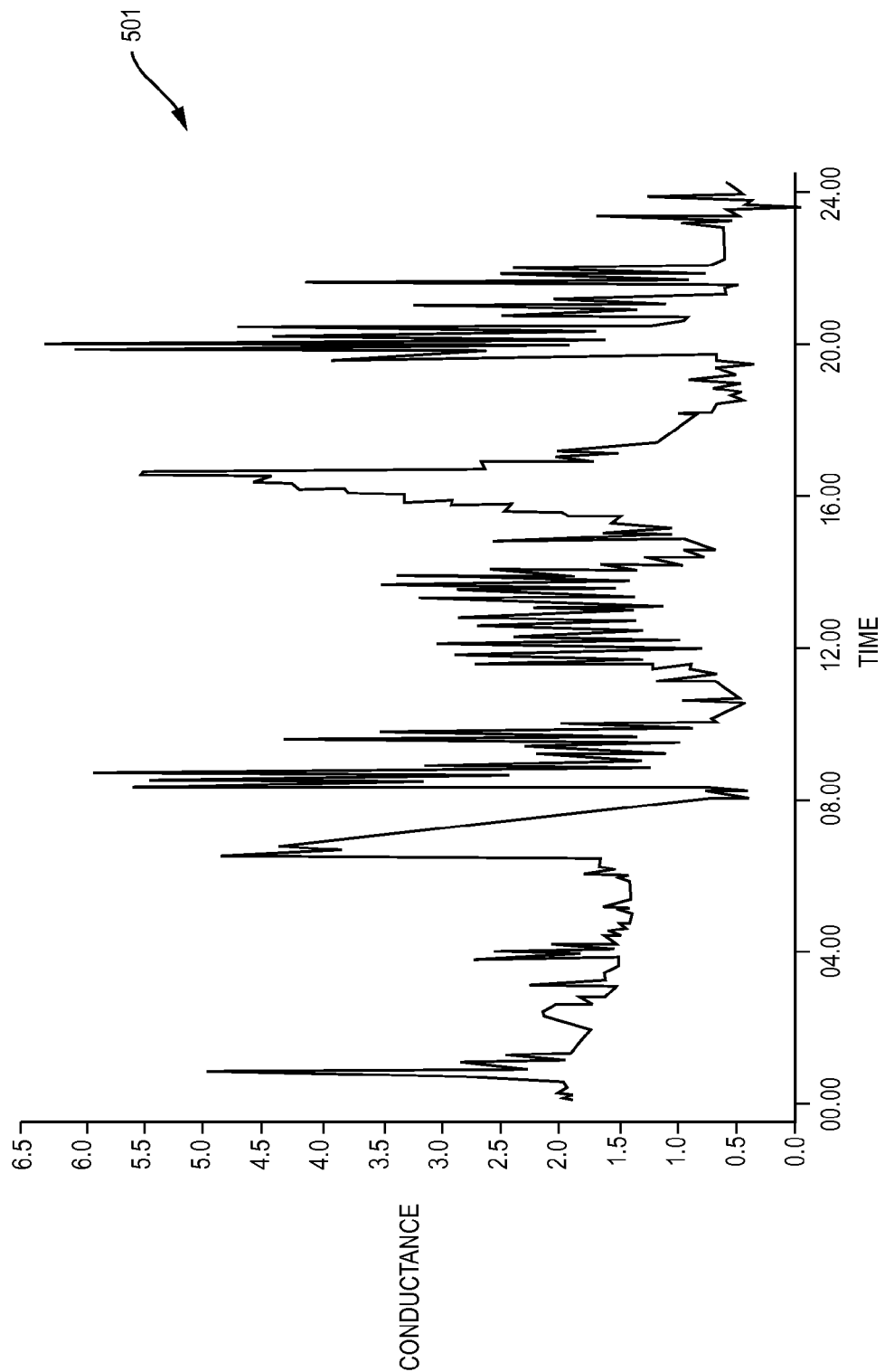
FIG. 15 shows three ways of displaying heart rate data for a 24 hour period.
Figure 15B:
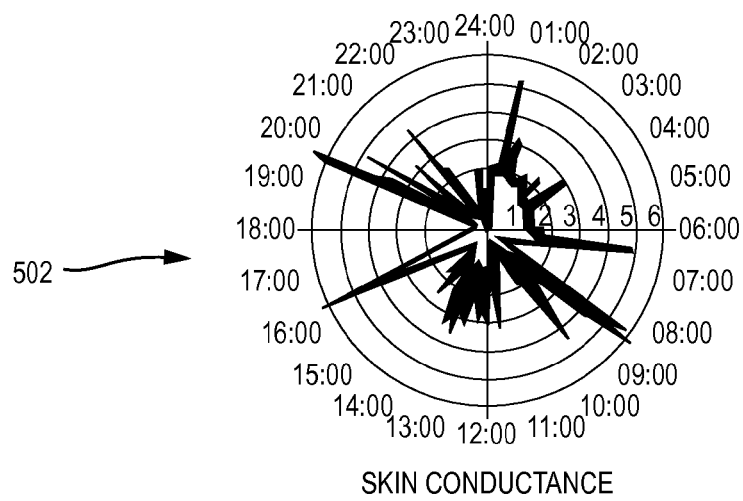
Figure 15C:
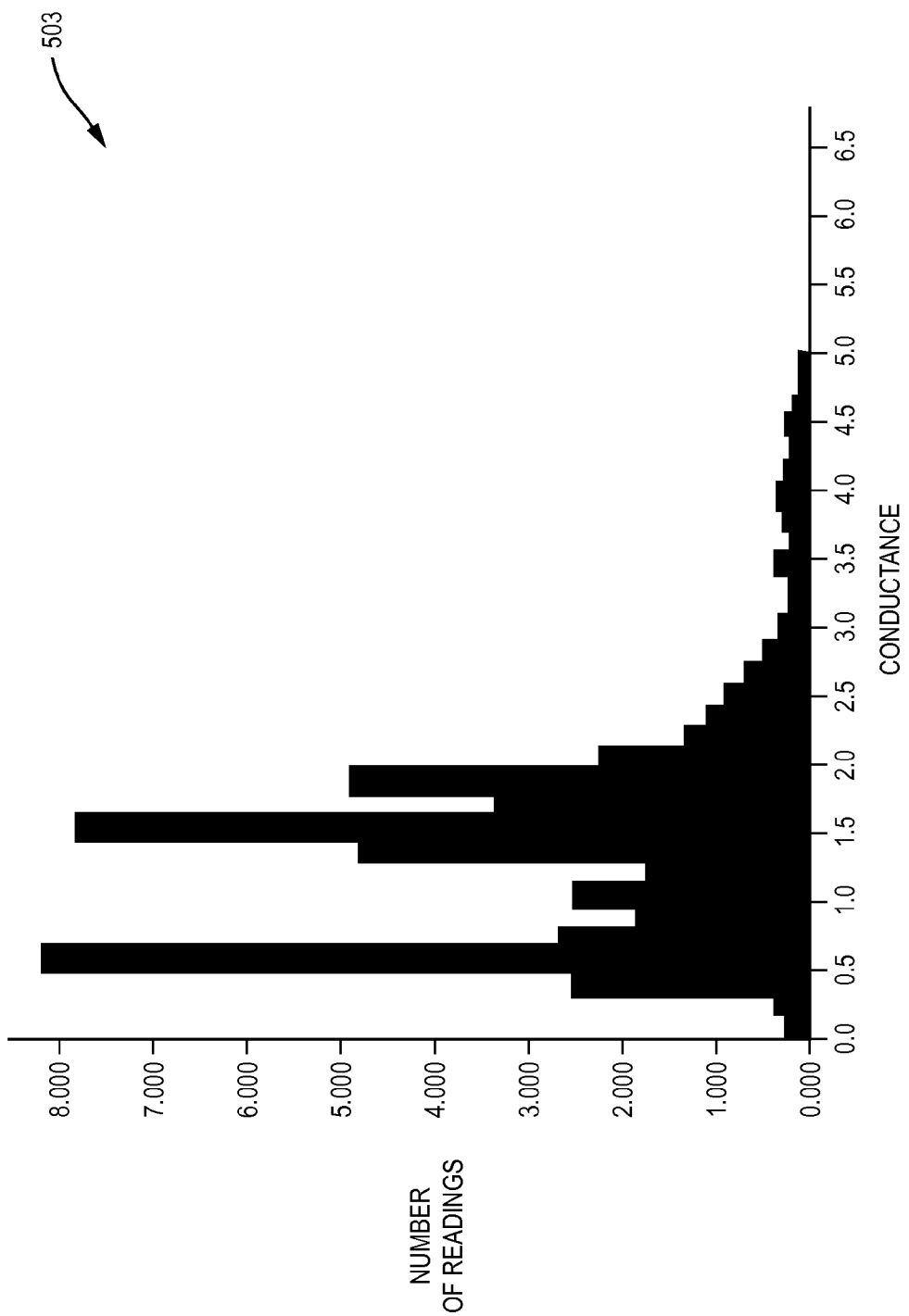

Alternatively, other server architectures, including databases and front end clients, may be used for the web site and the web site display and functionality may be different. The manner in which data is presented to users may vary. For example, FIG. 15 illustrates three different ways in which EDA data for a 24 hour period may be displayed: as a linear plot [501], polar plot [502] and histogram [503].

In addition to a computer device for receiving the data, the invention may have one or more data output devices used for displaying the data. The wireless transmission can be received by a mobile phone or other personal digital device, a computer, a favorite toy, or another wearable device.

Figure 16:
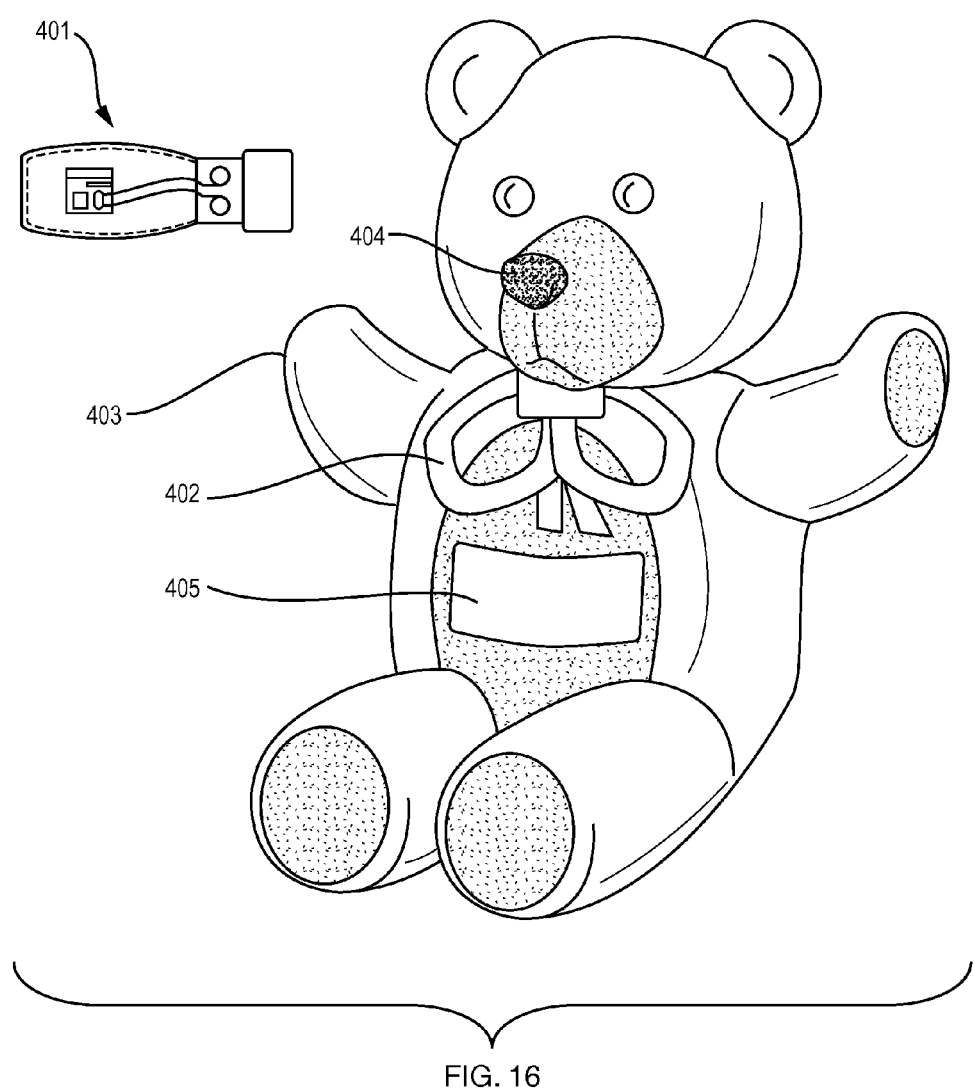
FIG. 16 shows a toy bear that displays data gathered by one or more sensors.

For example, FIG. 16 illustrates a toy that displays data received from a wearable device with a physiological sensor [401]. A glowing ribbon on the toy [402] contains a wireless transceiver and is programmed to change its change its color according to the physiology sensor information and patterns the wearer has specified interest in communicating. Alternatively, other glowing toy accessories (e.g., cape, necklace or bracelet) may be used. A force sensor [403] detects "shaking hands" with other toys. This allows the user to share the data beyond his or her individual toy in a way that involves a physical and easy to understand handshake agreement to share the data. An infrared transceiver [404] sends its own ID and receives its partner's ID when shaking hands is detected. Two toys can exchange their IDs so that they can share their physiology information. An LCD (liquid crystal display) screen [405] shows the sensor wearer's name or a chosen identifying tag.

Figure 20:
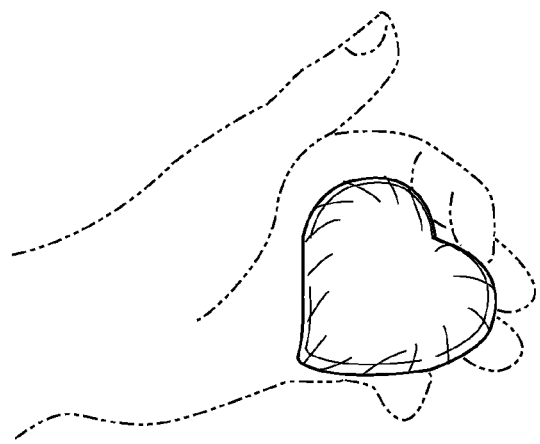
FIGS. 20-22 depict a hand-held device for delivering sensor data to a user who holds the device.
Figure 21:
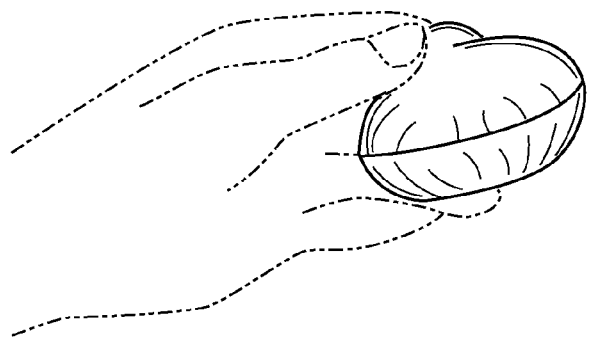

Embodiments of the present invention may employ a variety of data output devices for displaying and responding to the data. The wireless transmission can be received by a mobile phone or other personal digital device, a computer, a favorite toy, an alarm clock, or a wearable device. For example, a hand-held heart shape device illustrated in FIGS. 20-21 may wirelessly receive physiological signals and display heart rate information by means of a pulsing LED [451], an infrared LED [453] and/or may incorporate a vibratory motor [455] to produce a vibratory tactile vibration than can be sensed by the hand as seen in the block diagram, FIG. 22. An integrated circuit board including a micro-controller, radio module, the LED, the IR LED, and the vibrate motor may be concealed within the hand-held heart shaped device that is fabricated from a fabric having a soft surface texture.

Alternatively, the data received from the sensors may be rendered by one or more devices in any manner perceptible to the human senses, including auditory and tactile. Also, in some embodiments, alerts may be triggered by specified events (e.g., crossing certain thresholds) or patterns in such data. These alerts may be delivered to users in many ways, including e-mail, texting, instant messaging, and web syndication, including feed formats such as RSS (really simple syndication).

In one embodiment of the invention, the wireless sensor system is worn on the wrist (FIGS. 1 and 2) while the wearer's hands are free to operate a music device, play a video game or engage in another interactive entertainment experience. The sensor system transmits information related to the player's physiology or motion (e.g., calm, stressed, excited, hot and sweaty, or other measurable physiological state). The game or entertainment device can respond in ways that adapt the experience based on the physiological patterns, giving the wearer a different score or different experience based on their physiological state information or other physiologically based performance measures.

In another implementation of the invention, one or more consumers wear wrist or palm sensors that relay their physiological parameters while they interact with a product, display, advertisement, or sales promotion that is being evaluated for product feedback or for impact on customer attention and experience. The latter states can be detected through analysis of patterns in the physiological channels being transmitted.

In another embodiment of the invention, audience members in classrooms, distance-learning situations, stadiums, concert-halls, and other performance venues wear the system for communicating their excitement level. This usage provides live or logged audience feedback and can be used from remote audience members (e.g., over the Internet) as well as for co-present audience members (e.g., during a live sporting event). The group's overall excitement level might be displayed visually during the event, or stored for later analysis of how it changed throughout the event.

In another implementation of the invention, a group of two or more people gathered for dialogue or a shared experience may use the device to signal events during the discussion or shared experience (e.g. watching a video) to learn about where they respond similarly and differently. Thus the device enables comfortable hands-free measurement in situations such as therapy or inter-group dialogue, designed to enhance understanding of individuals' different perspectives and foster development of shared empathy.

In another instantiation of the invention, a wireless wrist-worn, hand-worn or foot-worn biosensor is used to monitor physiological patterns during sleep. The patterns can be logged for later analysis or interpreted in real time to determine and communicate information related to sleep stages (e.g. relating skin conductance to slow wave sleep spectral power, heart-rate variability and motion to REM sleep, as well as patterns of these, with temperature, to all the sleep stages). Thus the invention enables an easy-to-wear measure of sleep quality, sleep stages, sleep arousals, sleep efficiency, or sleep homeostasis, derived from physiological patterns sensed from the surface of the skin. This sensor allows some of the patient monitoring and research previously available only in labs to be carried out at home. The signal from this sensor may be received by technologies such as alarm clocks and sleep logs, forming a system that helps people better understand and manage their sleep and waking schedules.

Figure 24:
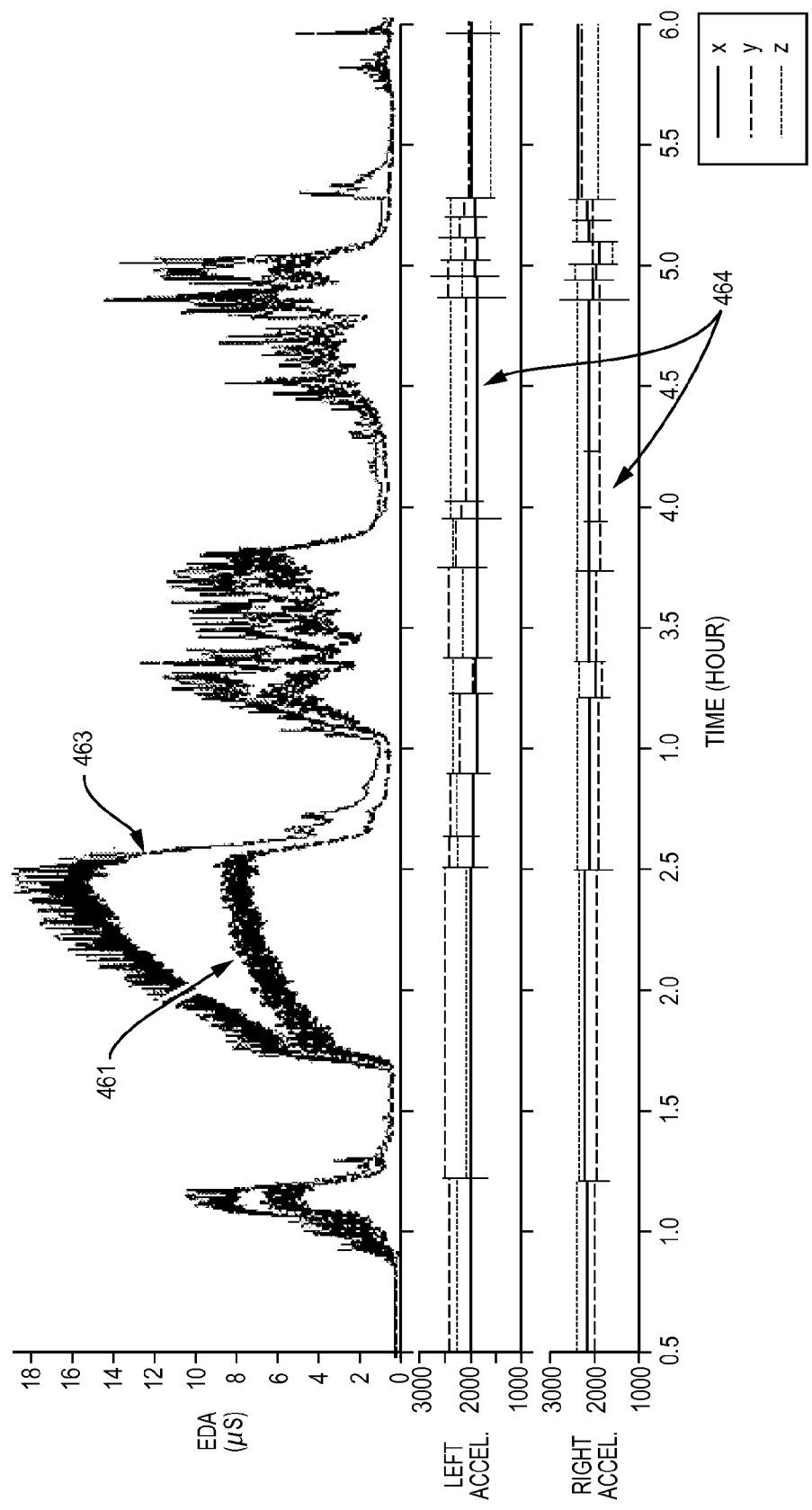
FIG. 24 is graphical presentation of data from two sensors worn simultaneously on left and right wrists indicating electrodermal activity during sleep.

FIG. 24 depicts a graphical presentation of data from two sensors worn simultaneously on left and right wrists as indicated at [461] and [463]. The charted graphs at [461] and [463] depict the electrodermal activity and the bottom graphs at 4[64] are 3-axis accelerometer signals. The horizontal axis is time sleeping.

In another embodiment of the invention, (FIG. 9) the wireless biosensor system is inserted into a soft form-fitting baby-toddler shoe plus sock, so that the electrodes are in contact with the sole and/or lower part of the leg and the data are used to learn about physiological changes during infant and child development. These changes are of interest as an alternate way to detect child arousal and attention, as well as to monitor for child anticipation, sleep patterns, autonomic regulation, and also a variety of mental and physical disorders that may affect autonomic nervous system activation on either one or both sides of the body. Specifically, one or more sensors may be advantageously employed to monitor physiological arousal in infants in order to predict, characterize, communicate and/or minimize infant crying behavior.

In another implementation of the invention, a person who has experienced multiple seizures (epilepsy) wears a sensor on one or both wrists with customized pattern recognition software in a tiny processor that analyzes patterns in autonomic nervous system activation to predict the onset of a seizure. This information can be communicated to a nearby helper, and may also be used to trigger various automatic interventions.

In another instantiation of the invention, the wearable device with both sensor and processor recognizes the wearer's detectable patterns of physiological change related to drug cravings such as the autonomic nervous system changes that happen in cue-triggered cocaine cravings. The wireless communication is sent to a PDA that provides a customized intervention triggered by these detected patterns. Those who wish to receive just-in-time support as part of their addiction treatment program wear this system.

In another embodiment of the invention, the wearable device with both sensor and processor recognizes the wearer's detectable patterns of physiological change related to threat such as the autonomic nervous system changes that happen in a bank robbery or other high-risk life-threatening situation. The device can be discretely integrated into clothing (wrist watch, shoe, etc.) so that it is not visible. The wireless components allow for multiple individuals (e.g. bank employees) to communicate their state simultaneously. The threat detection system, coupled with personalized feedback on a mobile device, can also be used to detect episodes in PTSD and deliver just in time therapeutic responses.

In another implementation of the invention, a person with limited verbal communication ability wears the wireless biosensor system to relay his or her internal physiological state parameters and these parameters' changes to another individual. The wearer maintains control over this communication, choosing to signal or not. The physiological patterns signal when a person might be excited, overloaded, stressed, nearing a meltdown or shutdown state, or experiencing an unseen state, such as pain. This embodiment of the system includes a device that the communication-impaired wearer can use for controlling when and with whom the information is shared. For example, the information could be shared as shown in FIG. 16, or shared by one or more cell phones or other personal digital devices.

In another embodiment, the present invention can be used to help analyze and highlight specific moments in a collection of recorded video data. In this embodiment, the present invention can be configured in the form of a wrist band that is worn by one or more spectators or observers during the course of a recorded event, such as a live musical performance, sporting event, theatrical show, television commercial or cinematic film. The physiological data from the observers is simultaneously recorded and can be used to measure the audience response. By measuring the level of audience response, it is possible to quickly identify and highlight important moments in the recorded event. Furthermore, if the present invention is worn by multiple users, it is possible to aggregate the physiological data from multiple users as a function of specific demographic parameters, such as age group, sex, political beliefs or socioeconomic status; this enables the ability to compare the audience response across different groups of users (e.g. men vs. women).

Figure 22:
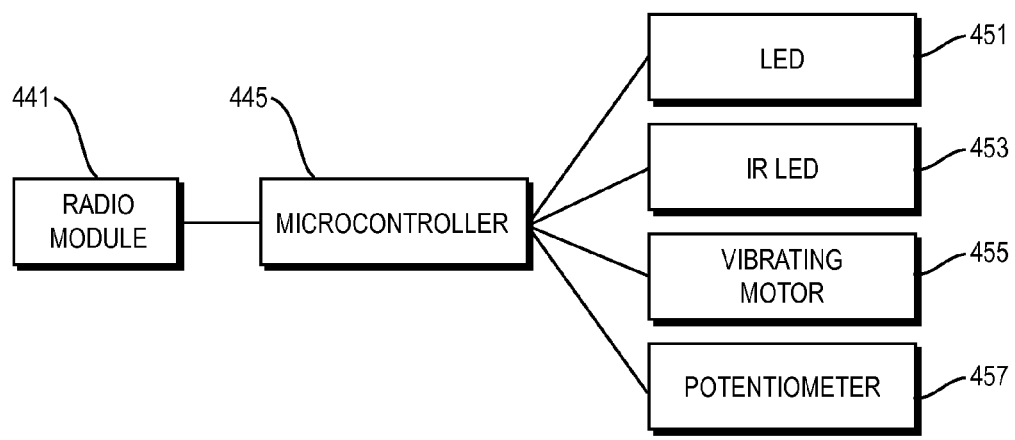
Figure 23:
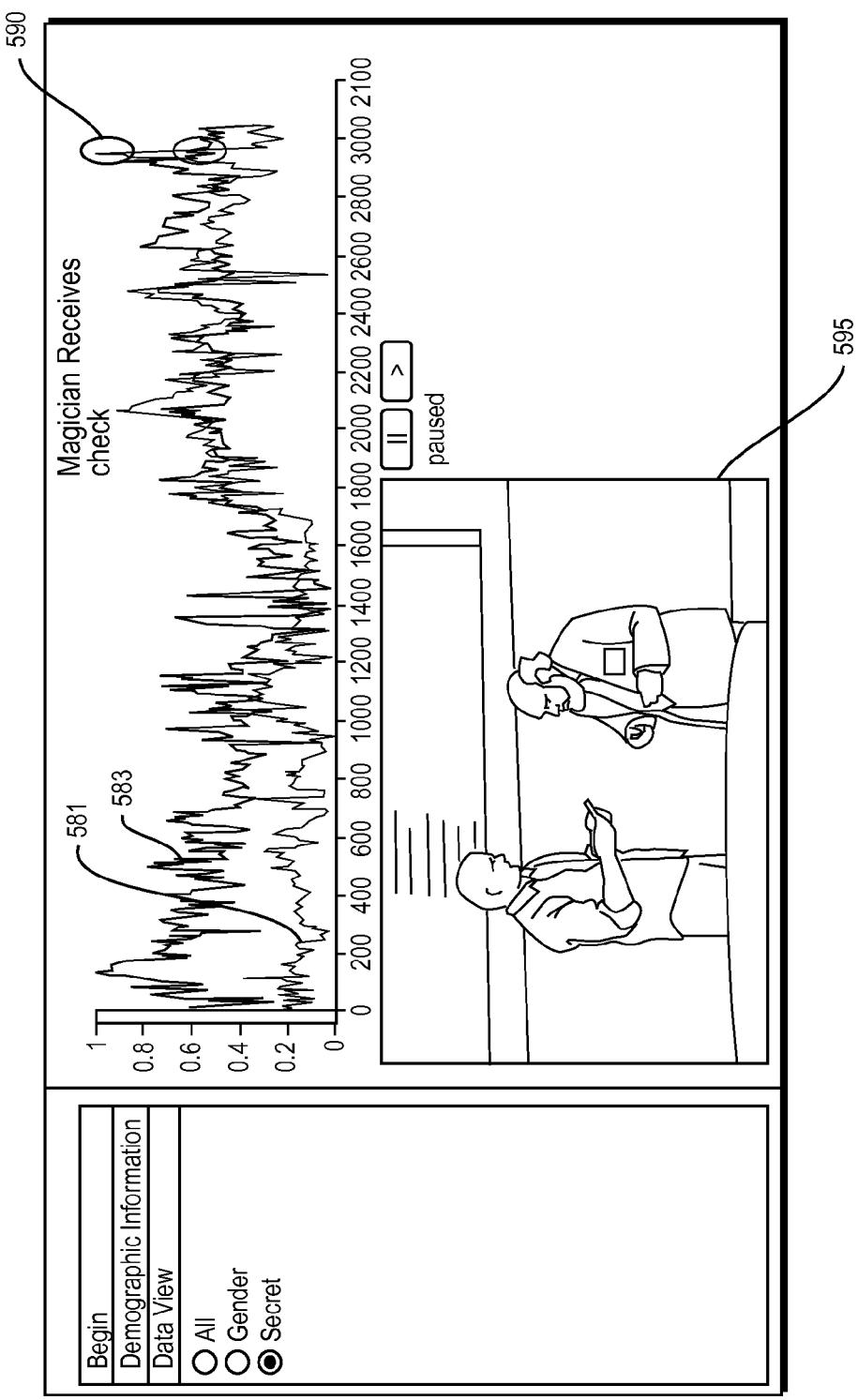
FIG. 23 illustrates a computer output screen for presenting graphs of sensor data indicative of the response of participants to a series of events and a mechanism for displaying a particular event which occurred when specific data was acquired.

FIG. 22 shows a plot of the aggregated physiological data for a group of people observing a performance of an event. In FIG. 2, the graph at [581] depicts data on a first measured audience response characteristic and the graph at [582] depicts a second measured audience response characteristic. Such a plot can be generated by a computer that analyzes the recorded video data for the event. The software allows users to view the data on a graph and select different ways of comparing aggregates (e.g., compare the reaction of all women to the entire group). Additionally, the graph allows the user to use the computer mouse to click on points of interest on the plot, such as the point in time seen at [590] when "a magician receives a check." Upon clicking on a particular point on the graph, the corresponding recorded video data is shown for that specific point in time as illustrated at [595]. This software can be used by researchers to analyze the audience response and address a number of challenges including: (1) the laborious task of monitoring interpersonal interactions within natural settings, and (2) the difficulty of expressing and sharing emotions with others. For the first, a researcher's attention can be drawn to emotionally charged moments within a collaborative setting. In this way, rather than having to start video analysis by viewing the entire recorded event, "high" points can be visually seen and visited immediately. Second, during videotaped interpersonal interactions, participants could review their encounter and provide personal insights into why they had the reaction they did. This can help the participants to reflect on and express emotions in ways that may not have been accessible otherwise.

Various embodiments of the invention, including those described above, may also be used by researchers studying human social interaction, communication, usability, developmental disability (e.g. interaction of physiological state with repetitive movements) or other human-human transactions, allowing a new ability to telemetrically monitor real-time changes in participants' arousal levels without encumbering the activity of participants. Other embodiments can be used to collect autonomic nervous system activity as an outcome measure in pharmaceutical trials.

CONCLUSION

It is to be understood that the methods and apparatus which have been described above are merely illustrative applications of the principles of the invention. Numerous modifications may be made by those skilled in the art without departing from the true spirit and scope of the invention.

What is claimed is:

1. A system for monitoring physiological data comprising:
a wearable washable breathable garment adapted to be worn in multiple positions on the human body;
a plurality of sensors attached to said garment for acquiring sensor data indicative of one or more of the following characteristics of said human body: heart rate variability, motion, electrodermal activity, and temperature, wherein at least one of said sensors is an electrodermal activity sensor that includes an op-amp circuit with non-linear feedback that automatically scales gain to compensate for a range in skin conductance;
a wireless communication unit attached to said garment for transmitting physiological data including or derived from said sensor data via a wireless communications link to a remotely located utilization system; and
a processor attached to said garment or included in said remotely located utilization system for analyzing said physiological data to identify patterns manifested by said physiological data indicative of the condition of said human body.

2. The system for monitoring physiological data set forth in claim 1 wherein said wearable washable breathable garment is a wrist band that may be positioned at different positions on the wrist or the palm of said human body.

3. The system for monitoring physiological data set forth in claim 1 wherein said wearable washable breathable garment is a sock, shoe or ankle band worn on or near the foot.

4. The system for monitoring physiological data set forth in claim 1 wherein said wearable washable breathable garment consists of an inner garment and an outer garment, wherein one or more of said sensors are attached to said inner garment in proximity to said human body and wherein all or part of said wireless communications unit is attached to said outer garment, and wherein said system further includes electrical connections coupling said sensors attached to said inner garment to said all or part of said wireless communications unit attached to said outer garment.

5. The system for monitoring physiological data set forth in claim 1 wherein said remotely located utilization system includes one or more radio receivers for receiving information from a plurality of remote sources including said wireless communications unit.

6. The system for monitoring physiological data set forth in claim 1 wherein at least one of said plurality of sensors includes one or more skin electrodes for measuring electrodermal activity.

7. The system for monitoring physiological data set forth in claim 6 wherein at least one of said plurality of sensors includes an oscillator whose oscillation frequency is dependent on skin conductance manifested by said human body and wherein said sensor data is indicative of the magnitude of said oscillation frequency.

8. The system for monitoring physiological data set forth in claim 6 wherein said skin electrodes comprise an electrically conductive fabric forming part of said washable wearable breathable garment.

9. The system for monitoring physiological data set forth in claim 1 wherein said utilization system includes a display for displaying information indicative of or derived from said physiological data.

10. The system for monitoring physiological data set forth in claim 7 wherein said utilization system includes a personal computer and wherein said display is coupled to and displays information produced by said personal computer by processing said physiological data.

11. The system for monitoring physiological data set forth in claim 7 wherein said utilization system includes a mobile telephone and wherein said display is coupled to and displays information received by said mobile telephone and relayed to said utilization device.

12. The system for monitoring physiological data set forth in claim 1 wherein said utilization system receives data concurrently from multiple remote sources.

13. The system for monitoring physiological data set forth in claim 1 wherein said utilization system is housed in a toy and includes a visible display or a sound output or both indicative of one or more attributes of said physiological data.

* * * * *